United States Patent [19]

Stapp

[11] 4,237,071

[45] Dec. 2, 1980

[54] OLEFIN OXIDATION PROCESS

[75] Inventor: Paul R. Stapp, Bartlesville, Okla.

[73] Assignee: Phillips Petroleum Company, Bartlesville, Okla.

[21] Appl. No.: 974,465

[22] Filed: Dec. 29, 1978

Related U.S. Application Data

[63] Continuation-in-part of Ser. No. 811,425, Jun. 29, 1977, Pat. No. 4,152,354.

[51] Int. Cl.$^3$ ............................................. C07C 45/34
[52] U.S. Cl. ................................... 568/401; 568/360
[58] Field of Search ................. 260/597, 597 B, 604 R

[56] References Cited

U.S. PATENT DOCUMENTS

| | | | |
|---|---|---|---|
| 3,020,293 | 2/1962 | Schönberg et al. | 260/604 R |
| 3,154,586 | 10/1964 | Bänder et al. | 260/597 B |
| 3,410,807 | 11/1968 | Lloyd | 260/597 B |
| 3,507,922 | 1/1976 | Gloyer et al. | 260/597 |
| 4,152,354 | 5/1979 | Stapp | 260/597 B |

OTHER PUBLICATIONS

Clement et al., Jour. Organic Chem., vol. 29, 1964, pp. 241-243.
Fahey, Jour. Organic Chem., vol. 39, pp. 3276-3277, 1974.

*Primary Examiner*—Werren B. Lone

[57] ABSTRACT

Olefins are oxidized to carbonyl compounds, for example, 1-hexene to 2-hexanone, with a Pd/Cu/alkali metal or alkaline earth metal chloride catalyst and a suitable surfactant in a diluent system comprising at least two liquid phases, wherein at least one liquid phase is an aqueous phase, in the presence of free oxygen. The addition of the surfactant to the system provides an improvement in olefin conversion and selectivity to the corresponding carbonyl compound. Suitable surfactants include, for example, quaternary ammonium halide compounds. Enhanced oxidation rates for the oxidation of internal olefins are obtained when one of the liquid phases of the diluent system is an alcohol phase.

8 Claims, No Drawings

OLEFIN OXIDATION PROCESS

This application is a continuation-in-part of co-pending application Ser. No. 811,425, filed June 29, 1977.

BACKGROUND OF THE INVENTION

This invention relates to the oxidation of olefinic carbon-carbon double bonds to carbonyl groups. In another aspect, it relates to the use of a diluent system comprising at least two liquid phases with at least one being aqueous. In another aspect, it relates to the use of a two-phase diluent system with one being an aqueous phase and another being an organic phase. In another aspect, this invention relates to a process for the oxidation of olefinic carbon-carbon double bonds in which a multi-phase diluent system is used with at least one phase being aqueous and at least one other phase being an alcohol. In still another aspect, this invention relates to an olefin oxidation process in which a two-phase diluent system is employed with one phase being aqueous and the other phase being an alcohol. In yet another aspect, it relates to the use of a Pd/Cu/alkali metal or alkaline earth metal chloride catalyst in conjunction with a multi-phase diluent system for the oxidation of olefinic carbon-carbon double bonds to carbonyl groups. In yet another aspect, this invention relates to the addition of a suitable surfactant to such a reaction system.

The Wacker-type oxidation of ethylene to acetaldehyde using a palladium chloride/cupric chloride/hydrochloric acid catalyst in an aqueous solution has been modified and applied to the synthesis of methyl ketones from terminal olefins. However, major problems have been encountered in using the Wacker-type oxidation in the oxidation of higher olefins. One problem is that of reduced rates of reaction due to the low solubility of the olefin in the aqueous medium. Another major problem is the concomitant secondary oxidation of the ketone product which leads to poor selectivities and poor yield of desired product.

SUMMARY OF THE INVENTION

The present invention, however, has solved the problems of the Wacker-type oxidation of higher olefins by resorting to "phase transfer" techniques and the addition of a suitable surfactant. The instant invention reacts the olefinic hydrocarbon reactant to be oxidized in the presence of free oxygen and a multi-phase diluent system, preferably a two-phase system with one phase aqueous and the other organic. The catalyst involved is a Pd/Cu/alkali metal or alkaline earth metal chloride catalyst with the palladium being either palladium or a palladium compound and the copper component being either a cuprous or cupric compound. It should also be noted that the HCl used in conventional Wacker oxidation reactions to maintain adequate conversion levels of the olefinic reactant is not part of the process of the present invention due to its deleterious effect on the oxidation reaction according to the instant invention. An alkali metal or alkaline earth metal chloride has been found, however, to favorably increase the selectivity of the instant invention. An additional component of the present invention, in a specified embodiment, which further increases the conversion and selectivity of the oxidation reaction is the addition of a suitable surfactant to the reaction system.

In another embodiment of this invention, the multi-phase diluent system comprises at least two phases with one phase being aqueous and another an alcohol phase. The use of an aqueous-alcohol multi-phase diluent system is particularly preferable when the olefinic reactant is an internal olefin such as 2-butene, 2-hexene, 3-hexene, and the like.

An object of the present invention, therefore, is to increase the conversion and selectivity of higher olefins in an oxidation process.

Another object is to increase the conversion and selectivity of higher olefins in an oxidation process by effectively removing the carbonyl compound product from the locus of the oxidation process.

Another object is the use of an improved diluent system in the oxidation of higher olefins.

Yet another object is to provide for the use of a reaction promoter for increasing the conversion and selectivity of an oxidation process for higher olefins.

Still another object of this invention is to provide a process with an enhanced rate of oxidation of internal olefins to carbonyl compounds using a particular multi-phase diluent system.

Other objects, aspects, and the several advantages of this invention will be apparent to those skilled in the art upon a study of this disclosure and the appended claims.

DETAILED DESCRIPTION OF THE INVENTION

The instant invention is concerned with a process for the conversion of olefinic carbon-carbon double bonds to carbonyl groups by oxidation of said olefinic compound in a reaction system comprising at least two liquid phases wherein at least one liquid phase is an aqueous phase. The instant invention is also concerned with a process for the conversion of olefinic carbon-carbon double bonds to carbonyl groups by oxidation of said olefinic compound in a reaction system comprising at least two liquid phases wherein at least one liquid phase in an aqueous phase and at least one liquid phase is an alcohol phase. The use of the alcohol phase is especially preferred in the oxidation of internal olefins.

In a specific embodiment of the instant invention, the oxidation process if carried out in the presence of a surfactant in order to increase the conversion and selectivity of the olefin reactant.

I. Olefinic Hydrocarbon Reactant

The olefinic hydrocarbon reactant oxidized according to the process of the instant invention is generally an acyclic olefinic compound containing at least 3 carbon atoms and having at least one olefinic carbon-carbon double bond or a cyclic olefinic compound containing at leasst 5 carbon atoms and having at least one olefinic carbon-carbon double bond. The preferred olefinic hydrocarbon reactant which is oxidized according to the process of the instant invention can be selected from the groups consisting of acyclic olefinic compounds containing from 3-20 carbon atoms per molecule and having 1, 2, or 3 olefinic carbon-carbon double bonds per molecule and cyclic olefinic compounds containing from 5-20 carbon atoms per molecule and having 1, 2, or 3 olefinic carbon-carbon double bonds per molecule. Within the limitations described above, suitable olefinic hydrocarbon reactants can be represented by the general formula RCH=CHR' wherein R and R' are selected from the group consisting of hydrogen, alkyl, alkenyl, alkadienyl, cycloalkyl, cycloalkenyl, and cycloalkadienyl radicals and wherein R can be the same or different from R' and wherein R and R' taken together can form an alkylene or alkenylene or alkadienylene radical thus forming a cyclic system. The term "olefinic carbon-carbon double bond" as used herein is not meant to include those carbon-carbon double bonds which are part of an aromatic carbocyclic system of alternating single and double bonds.

Examples of suitable monoolefinic compounds include: propylene, 1-butene, 2-butene, 1-pentene, 2-pentene, 1-hexene, 2-hexene, 3-hexene, 1-octene, 1-decene, 1-dodecene, 1-hexadecene, 1-octadecene, 1-eicosene, vinylcyclohexane, styrene, alpha-methylstyrene, cyclopentene, cyclohexene, cycloheptene, cyclooctene, cyclododecen, 3,3-dimethyl-1-butene, and the like.

Examples of suitable diolefinic compounds include 1,3-butadiene, 1,3-pentadiene, 1,5-hexadiene, 4-vinyl cyclohexene, 1,5-cyclooctadiene, 1,9-decadiene, 1,7-octadiene, 1,3-cycloheptadiene, and the like.

Examples of suitable triolefinic compounds include 1,5,9-cyclododecatriene, cycloheptatriene, 1,6-diphenyl-1,3,5-hexatriene, and the like.

It is preferred, however, that at least one olefinic carbon-carbon double bond is in the terminal position, i.e., the preferred olefinic reactant is a terminal olefinic hydrocarbon, since the oxidation rate of terminal olefinic bonds as compared to the oxidation rate of internal olefinic bonds is generally greater. When the olefinic reactant contains at least one internal double bond and it is desired to oxidize said internal bond, however, it is preferred that at least one phase of the multi-phase diluent system be an alcohol as it has been surprisingly discovered that the oxidation rate of internal olefinic carbon-carbon double bonds is greatly enhanced when an alcohol phase is used as compared to the use of other suitable organic phase diluents. It is also believed that terminal olefins which exhibit slow oxidation rates, e.g., higher molecular weight olefins, in other diluent systems will be oxidized at enhanced rates using an alcohol as at least one phase of the multi-phase diluent system.

II. Catalyst System

The catalyst utilized according to the instant invention for the oxidation of olefinic hydrocarbons to carbonyl compounds is made up of three components: (1) a palladium component, (2) a copper component, and (3) an alkali metal or alkaline earth metal chloride component.

(1) Palladium Component

The palladium component of the catalyst system of the instant invention can be palladium metal such as finely divided palladium powder or a palladium compound. Examples of suitable palladium compounds include allyl palladium chloride dimer $[C_3H_5PdCl]_2$, dichlorobis(triphenylphosphine)palladium(II), palladium(II) acetate, palladium(II) acetylacetonate, tetrakis(triphenylphosphine)palladium(0), palladium(II) chloride, palladium(II) iodide, palladium(II) nitrate, and the like. Mixtures of the above palladium compounds can also be utilized as the palladium component of the instant catalyst system if so desired.

(2) Copper Component

The copper component of the instant catalyst system can be provided by utilizing a cuprous or cupric compound or mixture thereof. A wide variety of copper compounds can be utilized to provide the copper component of the instant catalyst system. Specific examples of suitable copper compounds include copper (I) acetate, copper(II) acetylacetonate, copper(I) bromide, copper(I) chloride, copper(II) chloride, copper(I) iodide, copper(II) nitrate, and the like. Mixtures of suitable copper compounds can also be employed to provide the copper component of the instant catalyst system if so desired.

(3) Alkali Metal or Alkaline Earth Metal Chloride

The third component of the catalyst system of the instant invention is a chloride of an alkali metal or an alkaline earth metal. Specific examples of suitable alkali metal chlorides include lithium chloride, sodium chloride, potassium chloride, rubidium chloride, and cesium chloride. Examples of suitable alkaline earth metal chlorides include calcium chloride, barium chloride, strontium chloride, magnesium chloride, and beryllium chloride. Mixtures of the above metal chlorides can be employed as the third component of the catalyst system if so desired.

The ratios of the various catalyst components can be expressed in terms of a molar ratio of copper to palladium and a molar ratio of chloride ion derived from the alkali metal or alkaline earth metal chloride to palladium. The molar ratio of copper component to palladium component in the instant catalyst system is broadly from 1/1 up to 200/1 and preferably from 2/1 up to 50/1. The molar ratio of chloride ion derived from the alkali metal or alkaline earth metal chloride to palladium is broadly from 5/1 to 1,000/1 and preferably from 20/1 up to 400/1.

The amount of catalyst employed according to the instant invention can be expressed in terms of the molar ratio of olefinic hydrocarbon reactant to palladium component of the catalyst system. Broadly, the molar ratio of olefinic reactant to palladium component is from 5/1 up to 1,000/1 and preferably from 10/1 up to 250/1.

In a specific embodiment of the instant invention, the oxidation reaction is carried out in the presence of an additional surfactant component in order to increase conversion and selectivity of the olefin reactant. This additional surfactant component of the reaction system according to the instant invention is a compound selected from one of the five groups to be described more fully below. It will be recognized from the description of the five groups of compounds below that said compounds generally would be expected to exhibit surface-active properties, and, as such, they may be called surfactants. However, the term "surfactant" encompasses a very broad class of compounds, and it has been discovered that not all surfactants are suitable for use in the instant invention. Nevertheless, for convenience and simplicity, the suitable compounds that can be employed according to the instant invention and described more fully below will be termed surfactants herein. At the present time, it is not known whether these compounds behave as phase-transfer catalysts such as is taught in the art or whether they are functioning as micellar catalysts, a feature also disclosed in the prior art. Because of this uncertainty in the mode of action of these compounds in the instant invention and for convenience as mentioned above, the following compounds will merely be described herein as surfactants.

A suitable surfactant for use in the reaction system of the instant invention is selected from one of the five following groups:

(A) Quaternary ammonium salts of the general formula $(R''')_4N^+X^-$ wherein $R'''$ is an alkyl radical of from 1 to 20 carbon atoms and wherein the total number of carbon atoms in said quaternary ammonium salt is from 8 to 30 carbon atoms broadly and preferably from 16 to 22 carbon atoms; and wherein $X^-$ is selected from the group consisting of $Br^-$, $Cl^-$, $I^-$, $F^-$, $R'''CO_2^-$, $QSO_3^-$, $BF_4^-$, $HSO_4^-$ wherein Q is an aryl or alkaryl radical of 6 to 10 carbon atoms. It will be noted that a variety of anions are suitable as the $X^-$ component of the quaternary ammonium salts. Specific examples of quaternary ammonium salts according to the general formula given above include cetyltrimethylammonium(hexadecyltrimethylammonium) bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutylammonium fluoride, tetrabutylammonium tetrafluoroborate, and the like.

(B) Alkali metal alkyl sulfates of the general formula $R'^{\nu}OSO_3M$ wherein $R'^{\nu}$ is an alkyl radical of from 10 to about 20 carbon atoms and wherein M is an alkali metal. Examples of suitable compounds according to the general formula for the alkali metal alkyl sulfates include lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and the like.

(C) Alkali metal salts of alkanoic acids of the general formula $R'^{\nu}CO_2M$ wherein $R'^{\nu}$ and M have the same meaning as given above for the compounds of (B). Examples of suitable alkali metal salts of alkanoic acids include lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosenoate, potassium eicosenoate, and the like.

(D) Alkali metal salts of alkaryl sulfonic acids of the general formula

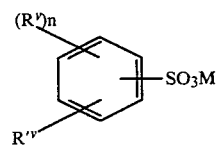

wherein $R'^{\nu}$ and M have the same meaning as given above and wherein $R^{\nu}$ is an alkyl radical of 1 to 4 carbon atoms and wherein n is 0 or an integer of from 1 to 4. Specific examples of compounds within the (D) group include sodium dodecylbenzenesulfonate, potassium dodecylbenzenesulfonate, lithium dodecylbenzenesulfonate, rubidium dodecylbenzenesulfonate, cesium dodecylbenzenesulfonate, sodium eicosylbenzenesulfonate, potassium dodecyltoluenesulfonate, sodium dodecylxylenesulfonate, and the like.

(E) 1-Alkyl pyridinium salts of the general formula

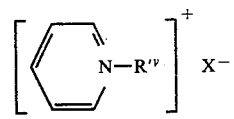

wherein $R'^{\nu}$ and $X^-$ have the same meaning as described above. Examples of suitable 1-alkyl pyridinium salts include 1-dodecylpyridinium para-toluenesulfonate, 1-dodecylpyridinium chloride, 1-hexadecylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and the like.

The amount of surfactant compound selected from groups (A) through (E) which is utilized according to the instant invention can be expressed in terms of a mole ratio based on the palladium component of the catalyst system. Broadly, the mole ratio of surfactant to palladium compound will be from 0.01/1 to 10/1 and preferably from 0.1/1 to 3/1.

III. Diluent System

As indicated above, the oxidation of the olefinic hydrocarbon according to the instant invention is carried out in the presence of a diluent comprised of at least two liquid phases (preferably only two), at least one of which is an aqueous phase. In a specific embodiment of the invention, it is preferred to carry out the reaction in the presence of a diluent comprised of at least two liquid phases, preferably only two, at least one of which is an aqueous phase and at least one of which is an alcohol phase when an olefinic reactant contains at least one internal double bond.

The nonaqueous phase will hereinafter be termed the organic phase. Said organic phase should be relatively inert to the oxidation conditions, of course, and also relatively inert to hydrolysis-type reactions. Furthermore, it is apparent that if at least two phases are present, at least one of which is an aqueous phase, that the organic diluent utilized must have somewhat limited solubility in the aqueous phase. Within these general requirements, a rather broad range of organic compounds can be utilized to form the organic phase according to the instant invention. Generally speaking, suitable compounds can be found in the classes of compounds described as aromatic hydrocarbons or alkyl-substituted aromatic hydrocarbons, halogenated aromatic compounds, alcohols, and esters of aromatic carboxylic acids although the latter may be less preferred because of a tendency toward hydrolysis of the ester group in certain instances. In addition, it has been found that compounds such as nitrobenzene and benzonitrile, commonly utilized as solvents for many organic reactions, show a definite inhibitory effect on the reaction of the instant invention presumably by complexing of one or more catalyst components. Specific examples of suitable organic diluents include cyclohexane, hexane, benzene, toluene, chlorobenzene, methylbenzoate, bromobenzene, 1,2,4-trichlorobenzene, ortho-dichlorobenzene, sulfolane, ortho-xylene, para-xylene, meta-xylene, methylcyclopentane, dimethyl ortho-phthalate, and the like. Mixtures of the above organic diluents may be utilized in some cases as desired. Generally speaking, the choice of the organic diluent may be often determined based on the difference in boiling points expected between the product of the oxidation reaction and the organic diluent so as to facilitate separation of the components of the reaction mixture.

When the olefinic reactant contains an internal double bond, it is preferred that the organic phase comprise an alcohol. The alcohol phase can be composed of a monohydric alcohol containing at least 3 and preferably from 3 to about 12 carbon atoms per molecule. Specific examples of suitable alcohols include 1-propanol, 2-propanol, 1-butanol, 2-methyl-1-propanol, 2-butanol, 2-methyl-2-propanol, 1-pentanol, 2-pentanol, 3-pentanol, 1-hexanol, cyclopentanol, cyclohexanol, cyclododecanol, 1-decanol, 2-decanol, 1-dodecanol, benzyl alcohol, and the like.

Mixtures of the above alcohol diluents can be utilized in some cases as desired. Generally speaking, the choice of the alcohol diluent can be often determined based on the difference in boiling points expected between the product of the oxidation reaction and the alcohol diluent so as to facilitate separation of the components of the reaction mixture.

The amounts of aqueous phase and organic diluent phase based on the starting olefinic reactant can vary over a wide range, and a suitable broad range includes from 20 to 0.2 volumes of organic diluent per volume of olefinic hydrocarbon reactant and preferably from 5 to 1 volumes of organic range diluent per volume of olefinic hydrocarbon reactant. Similarly, the broad range for the amount of aqueous phase is from 20 to 0.2 volumes per volume of olefinic hydrocarbon reactant and preferably from 5 to 1 per volume of olefinic hydrocarbon reactant. With respect to the use of an alcohol as the organic phase, the amount of the aqueous phase will range from about 0.2 to about 4 volumes per volume of alcohol phase and preferably from about 0.5 to about 2 volumes per volume of alcohol phase.

It is worth pointing out some predictions relating to the expected effects of the volume of aqueous phase on the oxidation reaction of the instant invention. First, if the aqueous phase volume becomes too small, the concentration of the catalyst components in the aqueous phase may cause a salting-out effect on the olefinic hydrocarbon reactant, thus greatly slowing down the reaction rate wherein the olefinic hydrocarbon reactant is oxidized to the desired carbonyl compound. Secondly, if the aqueous phase becomes too large, the concentration of catalyst components may be so dilute that the reaction with the olefinic hydrocarbon may also be greatly slowed. However, it can be seen that a judicious choice of the optimum amount of the aqueous phase for high conversion levels of the olefinic hydrocarbon reactant can readily be determined by a few well-chosen experiments.

At present, it is believed that the primary function of the organic phase in the reaction system of the instant invention is to greatly increase the selectivity to the desired carbonyl compound by effectively removing the carbonyl compound product from the locus of the oxidation reaction thereby preventing side reactions such as isomerization and/or further oxidation of the carbonyl compound. However, this explanation is to be treated merely as a theory of the mode of action of the organic phase in the reaction and the instant invention should not be bound to any extent by said theory.

IV. Oxygen

As indicated previously, the reaction of the instant invention is an oxidation reaction whereby an olefinic reactant is converted to a carbonyl compound in the presence of a catalyst and diluent system described above. Thus, the reaction of the instant invention is carried out in the presence of free oxygen. The oxygen may be supplied to the reaction mixture essentially as pure oxygen or admixed with other gases which are essentially inert to the reaction conditions. Air can be utilized as a source of oxygen for the oxidation reaction of this invention. As is generally true for most oxidation reactions, the reaction of the instant invention can be exothermic and thus some care should be exercised in the amount of oxygen present in the reaction system. For this reason and also to improve control of the temperature of the reaction, it is preferred to add oxygen or the gaseous mixture containing oxygen to the reaction zone incrementally such that explosive ranges of oxygen concentration do not develop. The pressure of oxygen utilized for the instant invention can broadly be from 2 up to 250 psig and preferably from 10 to 100 psig above the autogenous pressure at the temperature utilized.

V. Reaction Conditions

The temperature utilized in the instant invention is broadly from 20°–200° C. and preferably from 60°–150° C. It can also be noted that the particular temperature employed may be dependent somewhat on the olefinic hydrocarbon reactant. For example, at relatively high temperatures, a lower molecular weight olefinic hydrocarbon reactant may tend to be very insoluble in the aqueous phase of the two-phase system of the instant invention, thus causing a reduction conversion of the olefinic hydrocarbon reactant. On the other hand, a higher molecular weight olefinic reactant may be able to tolerate a higher reaction temperature and still maintain a reasonable degree of solubility in the aqueous phase and thus achieve a good degree of conversion at the higher temperature.

The time employed for the reaction according to the instant invention can vary over a wide range and will to some extent depend on the desired degree of conversion of the olefinic hydrocarbon reactant. Generally, a time period such as from 30 minutes to 8 hours will be employed in the instant invention.

Because the oxidation reaction according to the instant invention is carried out in the presence of a diluent system comprising at least two liquid phases, it is expected that good stirring will be of benefit and conventional means of achieving good agitation and contact between the liquid phases can be employed, as taught by the prior art.

The charge order of the reaction components and catalyst components is not particularly critical in the process of the instant invention. However, the presence of oxygen in the reaction mixture prior to heating of the mixture to the desired reaction temperature appears to promote higher selectivity to the desired carbonyl compound.

The process of the instant invention can be carried out in either a batch or continuous process.

Reaction vessels utilized in the process of the instant invention should, of course, be able to withstand the oxidizing conditions which are present. For this reason, glass-lined, tantalum, or titanium-clad vessels and conduits are recommended for use in the process of this invention.

VI. Reaction Mixture Workup

A variety of methods can be utilized to recover the products, unreacted olefinic hydrocarbon starting materials, and the catalyst in the aqueous phase in the instant invention. For example, the reaction mixture can be admixed with a saturated aqueous sodium chloride solution followed by extraction of the mixture into diethyl ether. The ether extract can then be distilled or treated in such a manner as to remove the ether leaving the organic residue containing the product and any unreacted olefinic hydrocarbon reactant. Said residue can then be subjected to fractional distillation procedures to recover the various components.

Another method of reaction mixture workup can involve fractional distillation of the entire reaction mixture to separate the components into various fractions and said distillation kettle bottoms can be recycled to the reaction zone as that portion containing essentially all of the catalyst system for the reaction.

Another method of treating the reaction mixture is to contact the entire mixture with a lower alkane such as n-pentane then separating the aqueous phase from the organic phase followed by fractional distillation of the organic phase to recover the products and any unreacted olefinic hydrocarbon reactants. The aqueous phase can be recycled to the reaction zone as described above since it contains essentially all of the catalyst components.

VII. Product Utility

As indicated earlier, the reaction of the instant invention provides a process for the conversion of olefinic hydrocarbon reactants to carbonyl compounds. Said carbonyl compounds are ketones. If the olefinic hydrocarbon reaction contains two carbon-carbon double bonds, the product can be an unsaturated monoketone or a diketone. Furthermore, the unsaturated monoketone can be recycled to the reaction zone for conversion to the diketone. Similarly a triolefinic reactant can be converted to intermediates such as unsaturated mono- or diketones and ultimately to a triketone. Ketones from the olefinic hydrocarbon reactants described in part I above have generally well-known utilities. For example, they can be utilized as solvents (methyl ethyl ketone) or as intermediates in the synthesis of other chemical compounds (pinacolone).

VIII. Examples

In all of the runs that are described in Examples I to XIV, the reaction vessel utilized in each of the runs was a 250 ml Fisher-Porter aerosol compatibility bottle equipped with a magnetic stirrer. Generally, the bottle was charged with the catalyst system, the diluents, and the olefinic reactant after which the bottle was placed in an oil bath, pressured to about 30 psig with oxygen, and then heated to the desired temperature. During the reaction period, the bottle was pressured intermittently at about 10–30 minute intervals to an oxygen pressure of about 80–120 psig. Usually the reaction mixture was recovered from the bottle reactor by cooling the reactor, venting the gas phase and pouring the mixture into about 500 ml of water. This mixture was then extracted into diethyl ether and the ether extract washed with water and dried over magnesium sulfate. The dried ether extract was then filtered and the ether stripped off in a distillation step. The residue remaining after the removal of the ether was then analyzed by gas-liquid phase chromatography. Significant deviations from the above general procedures will be noted where appropriate in the respective examples that follow.

EXAMPLE I

In a control run (Run 1), the 250 ml Fisher-Porter aerosol compatibility bottle was charged with 1-hexene (200 mmoles), methyl benzoate (50 ml), water (50 ml), palladium(II) chloride (5 mmoles), and cupric chloride (20 mmoles). The reactor was pressured to 80 psig (551 kPa) with oxygen and heated to 105° C. The reaction was continued for five hours with intermittent pressuring with oxygen as described above. Analysis of the reaction mixture by gas-liquid phase chromatography indicated a 55 percent conversion of 1-hexene with an 87 percent selectively to a mixture of hexanones, 55 percent 2-hexanone and 45 percent 3-hexanone.

Another control run (Run 2) was carried out under essentially the same conditions described above for Run 1 with the exception that 1.8 mmoles of hexadecyltrimethylammonium bromide was added to the reaction mixture. In this run (Run 2), a 64 percent conversion of 1-hexene was achieved with a 94 percent selectivity to hexanones, 62 percent 2-hexanone and 38 percent 3-hexanone.

Note that both runs did not employ an alkali metal or alkaline earth metal chloride catalyst component.

Hydrolysis of the methyl benzoate codiluent was observed in the above runs and caused some difficulty in product isolation.

The results of control Runs 1 and 2 described above indicate the improved olefin conversion and selectively to carbonyl compound products achieved in the oxidation of said olefinic reactant by the presence of a surfactant.

EXAMPLE II

A number of other runs were carried out utilizing 50 ml of chlorobenzene and 50 ml of water as the diluent system for the reaction. In these runs, 200 mmoles of 1-hexene was utilized as the olefinic hydrocarbon reactant, the temperature was 105° C. and the oxygen pressure was about 80 psig (551 kPa) with 5 mmoles of palladium(II) chloride. Each run also utilized 1.8 mmoles of hexadecyltrimethylammonium bromide as the surfactant component and a reaction period of 5–6 hours. Other components of the catalyst system utilized in the runs of this example and the results obtained in the runs (by gas-liquid phase chromatography analysis) are presented in Table I below.

TABLE I

| Run No. | $CuCl_2$, mmole | Alkali Metal Chloride Type | Alkali Metal Chloride mmole | 1-Hexene, Conv., % | Selectivity,[a] % | 2-Hexanone,[b] % |
|---|---|---|---|---|---|---|
| 3 | 20 | — | 0 | 51 | 99 | 68 |
| 4 | 40 | — | 0 | 59 | 100 | 94 |
| 5 | 100 | — | 0 | 83 | 92 | 96 |
| 6 | 20 | LiCl | 50 | 69 | 98 | 97.8 |
| 7 | 20 | LiCl | 100 | 73 | 100 | 98.8 |

TABLE I-continued

| Run No. | CuCl₂, mmole | Alkali Metal Chloride Type | Alkali Metal Chloride mmole | 1-Hexene, Conv., % | Selectivity,[a] % | 2-Hexanone,[b] % |
|---|---|---|---|---|---|---|
| 8 | 20 | LiCl | 200 | 25 | 91 | 99+ |
| 9 | 20 | NaCl | 50 | 72 | 100 | 98.5 |
| 10 | 20 | NaCl | 100 | 67 | 100 | 99+ |
| 11 | 20 | KCl | 100 | 69 | 99 | 99+ |
| 12 | 20 | CsCl | 50 | 75 | 94 | 98.4 |

[a] Selectivity to hexanones.
[b] Amount of 2-hexanone in ketone mixture.

Although the results shown for Run 5 appear to be quite good, the analysis of the product mixture revealed that production of chlorinated hexanones had become significant in this run. Thus, the needed additional chloride ion cannot be furnished by simply increasing the CuCl₂ level because of side reaction(s) such as chlorination of the product ketones.

The low conversion in Run 8 is believed to be due to a "salting out" effect of high salts concentration on the water-solubility of 1-hexene.

EXAMPLE III

Other runs were carried out utilizing the same apparatus and procedure as described above and utilizing the catalyst system shown for Run 7 of Table I in Example II. These runs of Example III examined the effect of changing the level of the surfactant, hexadecyltrimethylammonium bromide, in the reaction mixture. The results of these runs are presented in Table II below. Run 7 is included for convenience in comparing the results.

TABLE II

| Run No. | Surfactant, mmole | 1-Hexene, Conv., % | Selectivity,[a] % | 2-Hexanone,[b] % |
|---|---|---|---|---|
| 13 | 0 | 21 | 98 | 99+ |
| 7 | 1.8 | 73 | 100 | 98.8 |
| 14 | 3.6 | 75 | 82 | 99+ |

[a] See footnote [a] of TABLE I.
[b] See footnote [b] of TABLE I.

The results shown in Table II indicate the significantly higher conversion of hexene achieved according to the instant invention (Run 7) compared to that obtained in Run 13. Furthermore, it is shown in Run 14 that a doubling of the surfactant level did not significantly change the hexene conversion.

EXAMPLE IV

Two additional control runs for 1-hexene oxidation were carried out utilizing the catalyst system of Run 7 of Example II above in the same type of apparatus and with the same general procedure described in the earlier runs. Run 15 utilized 1.8 mmoles of hexadecyltrimethylammonium bromide as the surfactant component. However, Run 15 also utilized the addition of 60 mmoles of hydrogen chloride to the catalyst system. The addition of the HCl had a dramatic effect on the oxidation reaction. No oxygen uptake of the system was observed. This result is very different from that observed in the conventional Wacker oxidation reactions which require incremental additions of HCl to maintain adequate conversion levels of the olefinic reactant.

Run 16 utilized the same catalyst system as Run 7 described above, but, in this instance, employed N,N-dimethyl-1-hexadecanamine hydrochloride as the surfactant component rather than the quaternary ammonium bromide utilized in Run 7. Use of the tertiary amine salt in Run 16 drastically reduced the 1-hexene conversion from 73 percent to 6 percent under otherwise identical conditions. The result of Run 16 also points out the deleterious effect of acidic conditions on the oxidation reaction according to the instant invention.

EXAMPLE V

Additional control runs were carried out utilizing the same apparatus and general procedures previously described and the catalyst system of Run 7 described above with the exception that other alkali metal salts were utilized in the catalyst system rather than lithium chloride. These runs employed 5 mmoles of the palladium(II) chloride, 20 mmoles of cupric chloride, a 5-hour reaction time and 105° C. reaction temperature. As previously described, these runs also utilized 50 ml of chlorobenzene and 50 ml of water as the diluent system with 1.8 mmoles of hexadecyltrimethylammonium bromide as the surfactant component. The other alkali metal salts utilized in these runs are shown in Table III below along with the results obtained in said runs.

TABLE III

| Run No. | Alkali Metal Salt Type | Alkali Metal Salt mmole | 1-Hexene, Conv., % | Selectivity,[a] % | 2-Hexanone,[b] % |
|---|---|---|---|---|---|
| 17 | LiBr | 100 | 23 | 38 | —[c] |
| 18 | Li₂SO₄ | 100 | 14 | 100 | 72 |
| 19 | LiNO₃ | 100 | 63 | 65 | 86.4 |
| 20 | LiCl/LiNO₃ | 50/50 | 76 | 59 | 96.4 |

[a] See footnote [a] of Table I.
[b] See footnote [b] of Table I.
[c] Not determined.

The results of the above control runs (Runs 17–20) demonstrate that the use of alkali metal salts other than the chlorides provide significantly inferior results in the oxidation reaction according to the instant invention.

EXAMPLE VI

Other runs were carried out according to the instant invention utilizing a variety of organic compounds as the organic phase diluent according to the instant invention. These runs utilized the general conditions described above for Run 7 in terms of the amount of 1-hexene olefinic hydrocarbon reactant, catalyst system, surfactant amount and type, aqueous phase amount, reaction time and temperature. Two runs were included in this series (Runs 21 and 22) which were carried out without any organic diluent present in the system. The results of these runs and other runs of this example are shown below in Table IV. Run 7 is again included for ease of comparison of the results.

TABLE III

| Run No. | Organic Diluent Type | ml | 1-Hexene, Conv., % | Selectivity,[a] % | 2-Hexanone,[b] % |
|---|---|---|---|---|---|
| 21 | none | 0 | 92 | 76 | 98.6 |
| 22 | none[d] | 0 | 47 | 57 | 89.8 |
| 23 | toluene | 50 | 63 | 84 | —[c] |
| 24 | cyclohexane | 50 | 68 | 85 | 99+ |
| 25 | methyl benzoate | 50 | 58 | 100 | 99+ |
| 26 | benzonitrile | 50 | 20 | 84 | 83 |
| 27 | pyridine | 50 | 0 | — | — |
| 28 | sulfolane | 50 | 70 | 95 | 86 |
| 7 | chlorobenzene | 50 | 73 | 100 | 98.8 |

[a]See footnote [a] of Table I.
[b]See footnote [b] of Table I.
[c]See footnote [c] of Table III.
[d]Also contained no surfactant component.

It is apparent that solvents such as benzonitrile (Run 26) and pyridine (Run 27) are unsuitable as organic diluents for the oxidation reaction according to the instant invention. Presumably, such solvents inhibit or retard the oxidation reaction by a strong complexing of the palladium component in the organic phase. The use of sulfolane (Run 28) as the organic diluent gave good results but a tendency toward increased degree of isomerization, i.e., 14 percent of the ketone product was 3-hexanone. The use of methyl-benzoate (Run 25) is accompanied by some degree of hydrolysis of the organic diluent as previously mentioned in Example I.

EXAMPLE VII

Three runs were carried out according to the instant invention but which utilized internal olefins rather than 1-olefins as the olefinic hydrocarbon reactant in the oxidation reaction. These runs utilized the "standard" conditions previously described (Run 7) in terms of the reaction temperature, time, catalyst system, surfactant component, and diluent system. Run 29 utilized 2-hexene, Run 30 utilized cis-3-hexene, and Run 31 utilized trans-3-hexene. All three of the above runs gave less than 10 percent conversion of the olefinic reactant after five hours at 105° C. These results demonstrate the reduced reactivity of internal olefins in the oxidation reaction of the instant invention as compared to 1-olefins.

EXAMPLE VIII

The effect of reaction temperature on the oxidation of 1-hexene under otherwise "standard" conditions previously described (Run 7) was examined in a series of runs. The temperatures utilized in this series of runs and the reaction times employed are presented in Table V below. This table also presents the results obtained in the oxidation runs carried out as described.

TABLE V

| Run No. | Temp., °C. | Time, Hrs. | 1-Hexene, Conv., % | Selectivity,[a] % | 2-Hexanone,[b] % |
|---|---|---|---|---|---|
| 32 | 80 | 4.7 | 35 | 79 | 99+ |
| 7 | 105 | 5 | 73 | 100 | 98.8 |
| 33 | 125 | 5 | 84 | 78 | 99+ |
| 34 | 150 | 4 | 32 | 68 | 87 |

[a]See footnote [a] of Table I.
[b]See footnote [b] of Table I.

The product from Run 34 carried out at 150° C. contained 13 percent of 3-hexanone while the runs at lower temperatures (Runs 32, 7, and 33) gave ketone products consisting of essentially pure 2-hexanone. The nature of the by-products leading to the reduced selectivity to hexanones in Runs 32 and 33 was not determined but further oxidation to acids and the like may have occurred. It was somewhat surprising that the conversion in Run 34 was low but this may have been due to the lower olefin solubility in the aqueous reaction phase at the elevated temperature. It is presently believed that for a series of olefins there will be a reaction temperature at which conversion and selectivity are maximized. Said optimum temperature is probably different for each olefin in said series and can be easily determined with a few experiments.

EXAMPLE IX

Other runs were carried out according to the instant invention which examined the effect of initial oxygen pressure on the oxidation of 1-hexene carried out at 105° C. The otherwise "standard" conditions were used in these runs. In the runs of this example, the initial oxygen pressure was as indicated in Table VI and upon reaching the desired reaction temperature, the oxygen pressure was increased to 90 psig (620 kPa). When the oxygen pressure fell to about 60 psig (414 kPa), the reactor was repressured to about 90 psig (620 kPa). The results obtained in these runs are presented below in Table VI. Run 7 is again included for comparison.

TABLE VI

| Run No. | Initial $O_2$ Pressure, psig (kPa) | 1-Hexene, Conv., % | Selectivity,[a] % | 2-Hexanone,[b] % |
|---|---|---|---|---|
| 35 | 0 (0) | 73 | 83 | 99.3 |
| 7 | 30 (207) | 73 | 100 | 98.8 |
| 36 | 60 (414) | 77 | 99 | 99.4 |

[a]See footnote [a] of TABLE I.
[b]See footnote [b] of TABLE I.

In Run 35, above, wherein the reaction mixture was heated to 105° C. prior to the introduction of oxygen, the palladium chloride catalyst component had been reduced to palladium metal before the mixture achieved the desired reaction temperature. An explanation for the decrease in selectivity to hexanones in Run 35 is not known at present, but it is apparent that a positive oxygen pressure is beneficial in achieving high selectivities to the desired carbonyl oxidation products.

EXAMPLE X

Another series of runs was carried out utilizing 1-hexene as the olefinic hydrocarbon reactant and utilizing the previously described "standard" conditions, i.e., 200 mmoles of 1-hexene, the palladium (II) chloride/cupric chloride/lithium chloride (5/20/100 mmoles) catalyst system, 5-hour reaction time, 105° C. reaction temperature, and the usual procedure for adding oxygen. The runs of the instant series were carried out to examine a variety of compounds as the surfactant component of the reaction system. Previously described Runs 7, 14, and 16 are included in the results shown in Table VII below.

TABLE VII

| Run No. | Surfactant | 1-Hexene, Conv., % | Selectivity, %[a] | 2-Hexanone, %[b] |
|---|---|---|---|---|
| 7 | hexadecyltrimethylammonium bromide | 73 | 100 | 98.8 |
| 37 | sodium dodecylsulfate | 52 | 89 | 99+ |
| 38 | octadecanoic acid | 16 | 97 | 99+ |
| 39 | sodium octadecanoate | 31 | 95 | 97.6 |
| 40 | sodium dodecylbenzenesulfonate | 31 | 79 | 96 |
| 41 | Aliquat 336* | 25 | 80 | 99+ |
| 42 | tetraheptylammonium bromide | 30 | 83 | 100 |
| 43 | hexadecyltrimethylammonium octadecanoate | 78 | 90 | 100 |
| 16 | N,N-dimethyl-1-hexadecanamine hydrochloride | 6 | 100 | 99+ |
| 44 | 1-dodecylpyridinium p-toluenesulfonate | 85 | 87 | 98.5 |
| 45 | N,N-dimethyl-1-hexadecanamine | 26 | 100 | 97.9 |
| 46 | tetrabutylphosphonium chloride | 0 | — | — |
| 14 | none | 21 | 98 | 99+ |

*Aliquat 336-methyltrioctylammonium chloride.
[a]See footnote [a] of TABLE I.
[b]See footnote [b] of TABLE I.

The results shown in Table VII indicate that a variety of compounds can be utilized as the surfactant according to the process of the instant invention but that surprisingly a compound which has been known in the art as a "phase transfer catalyst," i.e., tetrabutylphosphonium chloride of Run 46, is not suitable as a surfactant component in the process of the instant invention.

EXAMPLE XI

Additional runs were carried out which examined the use of compounds other than alkali metal chlorides as a source of additional chloride ion for the catalyst system. These runs were carried out utilizing the otherwise "standard" conditions of the previous runs, such as 5 mmoles of palladium(II) chloride, 20 mmoles of cupric chloride, 1.8 mmoles of the surfactant hexadecyltrimethylammonium bromide, 50 ml of water, 50 ml of chlorobenzene, and five hours at 105° C. under the usual oxygen addition techniques. The results of these runs are presented in Table VIII shown below. Previously described Run 7 is included in the table for purposes of comparison.

TABLE VIII

| Run No. | Metal Chloride Type | mmole | 1-Hexene, Conv., % | Selectivity, %[a] | 2-Hexanone, %[b] |
|---|---|---|---|---|---|
| 7 | LiCl | 100 | 73 | 100 | 98.8 |
| 47 | NaCl | 100 | 67 | 100 | 99+ |
| 48 | CaCl$_2$ | 25 | 64 | 100 | 94.5 |
| 49 | CaCl$_2$ | 50 | 78 | 97 | 100 |
| 50 | CaCl$_2$ | 100 | 48 | 83 | 99+ |
| 51 | BaCl$_2$ | 50 | 79 | 96 | 100 |
| 52 | FeCl$_3$ | 33 | 22 | 55 | 71.0 |
| 53 | FeCl$_3$ | 50 | 8 | —[c] | 86.6 |

[a]See footnote [a] in Table I.
[b]See footnote [b] in Table I.
[c]See footnote [c] in Table III.

The results shown in Table VIII demonstrate that the alkaline earth metal chlorides at equivalent total chloride ion levels actually gave slightly higher conversion levels of the 1-olefinic hydrocarbon reactant than the alkali metal chlorides. However, selectivities for the alkaline earth metal chlorides under these conditions were slightly lower than that achieved with the alkali metal chlorides. It is also apparent that ferric chloride is unsuited as a source of the chloride ion in the catalyst component wherein an alkali metal or an alkaline earth metal chloride is utilized. In addition to the lower conversions and selectivities when utilizing the ferric chloride, there was also observed an appreciable amount of by-product which was believed to be 1-chloro-2-hexanone. The chlorinated ketone by-product is apparently not produced by free radical-type chlorination of the ketone product since treatment of 2-hexanone for five hours under the same conditions did not produce any chlorinated ketone. A possible explanation for the chlorinated ketone by-product is that the ferric chloride promoted allylic chlorination of the olefin reactant and that this chlorinated olefin was then oxidized to the chloroketone.

EXAMPLE XII

In the prior art description of the Wacker oxidation process, it is usually indicated that a wide variety of transition metal salts can be used as the cocatalyst to reoxidize the reduced palladium metal in the process. In the two-phase oxidation system of the instant invention such a wide variety of transition metal compounds has not been found suitable for the replacement of the cupric chloride catalyst component. For example, replacement of the cupric chloride catalyst component with cobalt chloride, stannous chloride, mercuric chloride, and ferric chloride gave reaction systems which were either extremely slow or completely inactive. In addition, attempts to substitute a variety of other compounds for the palladium(II) chloride catalyst component were also not very successful. For example, catalyst systems utilizing mercuric acetate, selenium dioxide, potassium permanganate, cerium trichloride, titanocene dichloride, uranyl chloride, molybdenum dioxide, thallium trichloride, and niobium pentachloride were all inactive in the two-phase oxidation system of the instant invention. Substitution of the palladium(II) chloride by platinum chloride provided a catalyst system which gave very low conversion in the oxidation of 1-hexene in the two-phase oxidation system of the instant invention, but this catalyst is believed to be impractical and too expensive for purposes of this reaction system.

The poor results achieved in all the runs described above in the instant example point out and rather clearly define the scope of the suitable catalyst components for use in the two-phase oxidation system of the instant invention whereby an olefinic hydrocarbon reactant is converted to a carbonyl compound.

EXAMPLE XIII

Another run (Run 54) was carried out according to the instant invention utilizing the same apparatus as previously described and the same catalyst system as described for Run 47 of Table VIII in Example XI. However, in the instant run, the surfactant material utilized was tetrabutylammonium bromide (1.8 mmoles)

rather than hexadecyltrimethylammonium bromide which was the surfactant utilized in Run 47. In other respects, the runs were essentially the same, i.e., 200 mmoles of 1-hexene was utilized as the olefinic hydrocarbon reactant and the diluent system was composed of 50 ml of water and 50 ml of chlorobenzene. The reaction temperature was 105° C. for a period of five hours, and, as previously described, oxygen was intermittently added to the reactor by repressuring the reactor to about 100 psig during the reaction period.

The reaction mixture was worked up by pouring the mixture into a saturated sodium chloride solution and then extracted into diethyl ether. The diethyl ether solution was dried over magnesium sulfate, filtered, and the ether removed by distillation to leave 85.5 grams of residue. Said residue was analyzed by gas-liquid phase chromatography as before which revealed the conversion of 1-hexene was 26.7 percent with a selectivity to hexanones of 100 percent and the amount of 2-hexanone in the ketone mixture was 98.3 percent. Comparison of the results of Run 54 with those of Run 47 indicate that tetrabutyl ammonium bromide was not as effective as hexadecyltrimethylammonium bromide in achieving good levels of 1-hexene conversion in the oxidation reaction carried out according to the instant invention.

EXAMPLE XIV

Two additional runs were carried out according to the instant invention wherein 1-hexene was oxidized utilizing the catalyst system of palladium chloride/cupric chloride/sodium chloride (5/20/100 mmoles) and 1.8 mmoles of hexadecyltrimethylammonium bromide as the surfactant material. These runs were carried out utilizing the 250 ml Fisher-Porter aerosol compatibility bottle equipped with a magnetic stirrer which was utilized in the previous runs. In each run, the reactor was pressured to 207 kPa (30 psig) with oxygen and heated to 105° C. with intermittent repressuring of the reactor with oxygen to about 689 kPa (100 psig) during the 5-hour reaction period. The two runs of this example varied the relative amounts of water and chlorobenzene utilized in the diluent system. Run 47 of Example XI is also included in the tabulation of results shown below in Table IX.

TABLE IX

| Run No. | Chlorobenzene, ml | Water, ml | 1-Hexene Conv., % | Selectivity,[a] % | 2-Hexanone,[b] % |
|---|---|---|---|---|---|
| 47 | 50 | 50 | 67 | 100 | 99+ |
| 55 | 75 | 25 | 11 | 100 | 96.7 |
| 56 | 25 | 75 | 72 | 71 | 99+ |

[a]See footnote (a) in Table I.
[b]See footnote (b) in Table I.

The results in Table IX show that the relative amounts of the aqueous and nonaqueous phases of the diluent system utilized according to the instant invention can have a significant effect on the conversion of the olefinic hydrocarbon reactant and can also affect the selectivity of the oxidation reaction to the desired carbonyl compounds.

In each of the runs in Examples XV and XVI, the reaction vessel utilized was a 250 ml Fischer-Porter aerosol compatibility bottle equipped with a magnetic stirrer. Generally, the bottle was charged with the catalyst system, the diluents and the olefinic reactant after which the bottle was placed in an oil bath, pressured to about 30 psig (207 kPa) with oxygen and then heated to the desired temperature. During the reaction period, the bottle was pressured intermittently at about 10-30 minute intervals to an oxygen pressure of about 80-120 psig (552-827 kPa). Usually the reaction mixture was recovered from the bottle reactor by cooling the reactor, analyzing the crude reaction mixture by gas-liquid phase chromatography for unreacted olefin, and pouring the mixture into about 50 ml of saturated aqueous sodium chloride solution. This mixture was then extracted into diethyl ether and the ether extract washed with water and dried over magnesium sulfate. The dried ether extract was then filtered and the ether stripped off in a distillation step. The residue remaining after the removal of the ether was then analyzed by gas-liquid phase chromatography. Significant deviations from the above general procedures will be noted where appropriate in the respective examples that follow.

The 2-butene utilized in the examples contains both cis- and trans-isomers. The olefins were introduced in the vapor phase.

EXAMPLE XV

A series of control runs were carried out to demonstrate the slow rate of reaction of internal olefins compared with terminal olefins when a diluent system such as chlorobenzene and water was used. In each run, the 250 ml. Fischer-Porter aerosol compatibility bottle was charged with 200 mmoles of 1-butene (runs 57 and 58) or 2-butene (runs 59 and 60), chlorobenzene (50 ml.) water (50 ml.), palladium(II) chloride (5 mmoles), cupric chloride dihydrate (20 mmoles), sodium chloride (100 mmoles), and hexadecyltrimethylammonium bromide (1.8 mmoles). The reactor was pressured to 30 psig (207 kPa) with oxygen and heated to the desired reaction temperature. The reaction was continued for 5 hours with intermittent pressuring with oxygen as described above. The results of the runs are shown in Table X.

TABLE X

| Run No. | Olefin | Reaction Temperature, °C. | Butene Conversion, % |
|---|---|---|---|
| 57 | 1-Butene | 90° | 95 |
| 58 | 1-Butene | 75° | 92 |
| 59 | 2-Butene | 90° | 31 |
| 60 | 2-Butene | 75° | 13 |

The results of these runs show that at both 90° and 75° C., the conversion of the starting butene with a chlorobenzene-water diluent system is much less for the internal olefin (2-butene) than for the terminal olefin (1-butene) under the same reaction conditions.

EXAMPLE XVI

Several runs were carried out with a diluent system containing water and a variety of alcohols and at several reaction temperatures. In each run, the reaction vessel was charged with 2-butene (200 to 212 mmoles), an alcohol diluent (50 ml), water (50 ml), palladium(II) chloride (5 mmoles), cupric chloride dihydrate (20 mmoles), sodium chloride (100 mmoles), and hexadecyltrimethylammonium bromide (1.8 mmoles). Each run was conducted for a reaction time of 5 hours. The alcohol diluent and reaction temperature utilized in each run and the results obtained in the runs (by gas-liquid chromatographic analysis) are presented in Table XI below. Run 60 from Example XV is included for comparison.

TABLE XI

| Run No. | Diluent | Reaction Tem., °C. | 2-Butene Conv., % | Selectivity mole %[a] |
|---|---|---|---|---|
| 60 | Chlorobenzene | 75° | 13 | 95 |
| 61 | Ethanol | 75° | 10 | — |
| 62 | 1-Propanol | 75° | 65 | 100 |
| 63 | 1-Butanol | 60° | 38 | 100 |
| 64 | 1-Butanol | 75° | 79 | 85 |
| 65 | 1-Butanol | 80° | 82 | 80 |
| 66 | 1-Hexanol | 75° | 50 | 81 |
| 67 | Cyclohexanol | 75° | 66 | 98 |

[a] Selectivity to methyl ethyl ketone based on the amount of 2-butene reacted.

The results of the runs in Table XI demonstrate the increase in 2-butene conversion of the invention runs 62 through 67 with several different alcohols and water as the diluent system over the control run 60 with chlorobenzene and water as the diluent system. Very little oxygen uptake was observed in run 61 with an ethanol-water diluent system. Since little oxidation had occurred, the reaction vessel was vented and the contents discarded. The poor result of the run with an ethanol-water diluent system is believed to be a result of the high solubility of ethanol and water and the resulting inability to form two phases.

Reasonable variations and modifications which will become apparent to those skilled in the art can be made in the present invention without departing from the spirit and scope thereof.

I claim:

1. In a process for the conversion of the olefinic carbon-carbon double bonds of an olefinic hydrocarbon reactant to ketone carbonyl groups by contacting an olefinic hydrocarbon selected from the group consisting of (a) acyclic olefinic compounds containing 3–20 carbon atoms per molecule and having 1, 2, or 3 olefinic carbon-carbon double bonds per molecule and (b) cyclic olefinic compounds containing 5–20 carbon atoms per molecule and having 1, 2, or 3 olefinic carbon-carbon double bonds per molecule with a reaction system comprising:

oxygen;
a diluent comprising at least two liquid phases including an aqueous phase and an organic phase;
a catalyst comprising:
(1) palladium,
(2) copper, and
(3) an alkali metal or alkaline earth metal chloride; and a surfactant selected from the group of:
(1) quaternary ammonium salts of the general formula $(R''')_4N^+X^-$,
(2) alkali metal alkyl sulfates of the general formula $R'^vOSO_3M$,
(3) alkali metal salts of alkanoic acids of the general formula $R'^vCO_2M$,
(4) alkali metal salts of alkaryl sulfonic acids of the general formula

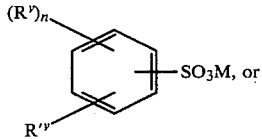

(5) 1-alkyl pyridinium salts of the general formula

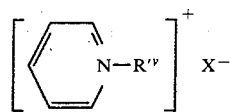

wherein $R'''$ is an alkyl radical of from 1 to 20 carbon atoms and wherein the total number of carbon atoms in said quaternary ammonium salt is from about 8 to about 30 carbon atoms; $X^-$ is selected from the group consisting of $Br^-$, $Cl^-$, $I^-$, $F^-$, $R'''CO_2^-$, $QSO_3^-$, $BF_4^-$, $HSO_4^-$ wherein Q is an aryl or alkaryl radical of 6 to 10 carbon atoms; $R'^v$ is an alkyl radical of from 10 to about 20 carbon atoms; M is an alkali metal; $R^v$ is an alkyl radical of 1 to 4 carbon atoms and wherein n is 0 or an integer of from 1 to 4, whereby the reaction is conducted under such conditions of temperature and pressure that oxidation of the olefinic hydrocarbon reactant takes place, the improvement comprising using as said organic phase an alcohol having 3 to about 12 carbon atoms.

2. A process as in claim 1 wherein:
the molar ratio of copper to palladium is about 1:1 to about 200:1;
the molar ratio of the alkali metal or alkaline earth metal chloride to palladium is about 5:1 to about 1,000:1;
the molar ratio of said olefinic hydrocarbon reactant to palladium is about 5:1 to about 1,000:1;
the molar ratio of said surfactant to palladium is about 0.01:1 to about 10:1;
said free oxygen is supplied by the use of air and the pressure of oxygen in the reaction system is in the range of from about 2 to about 250 psig above the autogeneous pressure at the temperature utilized; and
said reaction temperature is in the range of about 20° C. to about 200° C.

3. A process as in claim 1 wherein said alcohol is a monohydric alcohol containing at least 3 carbon atoms.

4. A process as in claim 3 wherein the amount of alcohol phase of the two-phase diluent is in the range of about 20 to about 0.2 volumes of alcohol to one volume of olefinic hydrocarbon reactant and the amount of aqueous phase is in the range of about 20 to about 0.2 volumes per volume of olefinic hydrocarbon reactant and from about 0.2 to about 4 volumes per volume of alcohol phase.

5. A process as in claim 1 wherein said olefinic hydrocarbon reactant is an internal olefin.

6. A process as in claim 5 wherein said olefinic hydrocarbon reactant is 2-butene.

7. A process as in claim 3 wherein said alcohol diluent is n-butanol.

8. A process as in claim 1 wherein:
said diluent comprises two phases with one phase being aqueous and the other being an alcohol with the alcohol being n-butanol;
said olefinic hydrocarbon reactant is 2-butene;
said catalyst is palladium(II) chloride, cupric chloride, and sodium chloride; and
said surfactant is hexadecyltrimethylammonium bromide.

* * * * *

UNITED STATES PATENT AND TRADEMARK OFFICE
CERTIFICATE OF CORRECTION

PATENT NO. : 4,237,071

DATED : December 2, 1980

INVENTOR(S) : Paul R. Stapp

It is certified that error appears in the above-identified patent and that said Letters Patent are hereby corrected as shown below:

Column 19, line 49, after "and" there should be a paragraph.

Column 19, line 51, "$(R''')_4N+X-$" should be --- $(R''')_4N^+X^-$ ---.

Column 20, line 5, "X-" should be --- $X^-$ ---.

Column 20, line 11, "X-" should be --- $X^-$ ---.

Column 20, lines 12 & 13, "Br-, Cl-, I-, F-, $R'''CO_2-$, $QSO_3-$, $BF_4-$, $HSO_4-$" should be --- $Br^-$, $Cl^-$, $I^-$, $F^-$, $R'''CO_2^-$, $QSO_3^-$, $BF_4^-$, $HSO_4^-$ ---.

Signed and Sealed this

Twenty-eighth Day of July 1981

[SEAL]

Attest:

GERALD J. MOSSINGHOFF

Attesting Officer    Commissioner of Patents and Trademarks